United States Patent [19]

Suzuki

[11] 4,308,397

[45] Dec. 29, 1981

[54] PREPARATION OF ALKYL ALKOXYACETATES

[75] Inventor: Shigeto Suzuki, San Francisco, Calif.

[73] Assignee: Chevron Research, San Francisco, Calif.

[21] Appl. No.: 139,610

[22] Filed: Apr. 11, 1980

Related U.S. Application Data

[63] Continuation of Ser. No. 22,017, Mar. 19, 1979, abandoned.

[51] Int. Cl.$^3$ .............................................. C07C 51/12
[52] U.S. Cl. ................................................. 560/187
[58] Field of Search ............................... 560/179, 187

[56] References Cited

U.S. PATENT DOCUMENTS 2,211,625  8/1940  Loder ................................. 560/179
3,948,977  8/1976  Suzuki ............................... 560/187

*Primary Examiner*—Natalie Trousof
*Assistant Examiner*—Leah Hendriksen
*Attorney, Agent, or Firm*—J. A. Buchanan, Jr.; T. G. DeJonghe; C. J. Caroli

[57] ABSTRACT

Alkyl alkoxyacetates from $C_3$–$C_6$ secondary alcohols, formaldehyde and carbon monoxide at a temperature of 5° C. to −20° C. and a carbon monoxide pressure of 0.5 to 275 atm.

5 Claims, No Drawings

PREPARATION OF ALKYL ALKOXYACETATES

This is a continuation of application Ser. No. 22,017, filed Mar. 19, 1979, now abandoned.

BACKGROUND OF THE INVENTION

The present invention relates to a process for producing an alkyl alkoxyacetate from a secondary alcohol by reacting said secondary alcohol with carbon monoxide and formaldehyde. U.S. Pat. No. 3,948,977 teaches the preparation of an alkyl alkoxyacetate by reacting a $C_1$-$C_{20}$ primary alcohol or mixtures thereof with carbon monoxide and formaldehyde in the presence of hydrogen fluoride catalyst. Temperatures of reaction are stated to be in the range of 0° to 100° C., and the carbon monoxide pressure in the range 10 to 4000 psig (0.68 to 272 atmospheres). Alkyl alkoxyacetates are known to be useful as solvents.

SUMMARY OF THE INVENTION

It has now been found that alkyl alkoxyacetates can be prepared from secondary alcohols, as opposed to primary alcohols, by reacting carbon monoxide, formaldehyde and secondary alcohols of not more than 10 carbon atoms in the presence of hydrogen fluoride catalyst, the temperature of reaction being in the range 0° C. to −30° C., preferably −5° C. to −20° C. In carrying out the reaction, the partial pressure of the carbon monoxide is about in the range 0.5 to 275 atmospheres, preferably 2 to 100 atmospheres.

As indicated, the present invention is based on the surprising discovery that in order to produce the alkyl alkoxyacetates from the corresponding secondary alcohols, reaction temperatures substantially lower than those that prevail in producing the prior art alkyl alkoxy acetates from the corresponding primary alcohols must be used. Thus, while temperatures of the order of 25° C. to 50° C. appear to be optimum in producing alkyl alkoxyacetates from primary alcohols, such temperatures are considerably above the operable range of 0° C. to −30° C. characterizing the preparation of alkyl alkoxyacetates from secondary alcohols.

DETAILED DESCRIPTION OF THE INVENTION

The secondary alcohols contemplated herein to produce the corresponding alkyl alkoxyacetates, useful as solvents, contain not more than 10 carbon atoms, and preferably not more than 6 carbon atoms. They may be represented by the formula

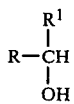

where R and $R^1$ are the same or different alkyl groups of 1 to 8 carbon atoms, provided that the sum of the two is not greater than 9. Specific examples of suitable alcohols are isopropyl alcohol (2-propanol), 2-butanol, 2-pentanol, 3-pentanol, 3-hexanol, 2-heptanol, 2-octanol, 3-octanol, 4-octanol, 4-nonanol and 5-decanol.

In producing the alkyl alkoxyacetates of the present invention, the proportions of alcohol and formaldehyde are fed to the reaction zone in an alcohol to formaldehyde mol ratio in the range 2–15 mols of alcohol for each mol of formaldehyde, the preferred ratio being 2.5 mols of alcohol for each mol of formaldehyde. The carbon monoxide fed to the reaction zone is in an amount sufficient to effect during reaction a carbon monoxide partial pressure of 0.5 to 275 atmospheres, preferably 50 to 70 atmospheres. An amount of hydrogen fluoride effective to catalyze the reaction is used, and can vary over a wide range. Thus, amounts of hydrogen fluoride in a mol ratio of 5 to 20 for each mol of formaldehyde, preferably 8 to 15 mols of hydrogen fluoride for each mol of formaldehyde will be found satisfactory. Water in an amount in the range of 0 to 0.1 mols per mol of alcohol may also be present in the feed.

The reaction time decreases with increased temperature. In the range of −20 to 0° C. the reaction is essentially finished in less than 30 minutes, usually within 10 to 20 minutes. Longer times are required for reactions below this temperature range. As will occur to those skilled in the art, reaction is deemed to be complete upon the carbon monoxide pressure reaching a stabilized value after drafting from the initial pressure.

At temperatures in the range of −5° C. to 0° C. yields fall off regardless of reaction time. It is theorized that the secondary alcohol undergoes side reactions, such as dehydration, and hence is not available for forming the desired alkoxyacetate. Therefore, the preferred temperature range is from −5° C. to −20° C.

The esters produced by this process are recovered from the reaction mixture by first removing the hydrogen fluoride as a gas under reduced pressure at temperatures no higher than 25° C. This crude product is then dissolved in a water-immiscible, low boiling organic solvent such as diethyl ether, or methyl acetate. The resulting solution is washed with an aqueous base, e.g. aqueous sodium bicarbonate; and after drying the solvent is removed by distillation or evaporation. The crude product obtained in this way is satisfactory for many uses, but it may be further purified by distillation, preferably at reduced pressure. An alternative recovery scheme involves quenching the reaction by adding ice water, then neutralizing and extracting with a solvent and finishing up as before.

The following examples are given further to illustrate practice of the invention.

EXAMPLE 1

A 300-ml magnetically stirred stainless-steel autoclave was charged with 6 grams of trioxane (0.2 mols of formaldehyde equivalents), 30 grams of isopropyl alcohol (0.5 mols) and 50 grams of hydrogen fluoride (2.5 mols). The autoclave was sealed and pressured to 68 atmospheres with carbon monoxide at −15° C. The temperature was held at this level for 90 minutes during which time the contents were stirred continuously. The carbon monoxide pressure dropped rapidly and in less than 30 minutes, it reached its final pressure.

After warming to room temperature, analysis by gas chromatography showed complete conversion of formaldehyde and a greater than 95% yield of isopropyl isopropoxyacetate.

EXAMPLE 2

The procedure of Example 1 was repeated, except that the initial temperature was −10° C. Again the carbon monoxide pressure drop occurred within less than 30 minutes, and steadied at 54 atmospheres, at a final temperature of −15° C. Gas chromatography analysis showed complete formaldehyde conversion and over 95% yield of isopropyl isopropoxyacetate.

A portion of the reaction product was diluted with an ice-water mixture, and then extracted with ether. A gas chromatography analysis of the ether extract gave a 70% yield of ester along with a 20% yield of isopropoxyacetic acid. Evaporation of the ether gave a crude isopropyl isopropoxyacetate product.

EXAMPLE 3

The procedure of Example 1 was repeated, but at −30° C. After 5 hours of reaction, the pressure reached the calculated final value, and the reaction was terminated. The reaction mixture was diluted with an aqueous sodium carbonate and then extracted with ether. The ether extract upon evaporation gave 32% yield of isopropyl isopropoxyacetate.

EXAMPLE 4

This reaction was carried out the same as in Example 2, except that the temperature of reaction was maintained at −10° C. The carbon monoxide uptake was completed in about 30 minutes, to give a final pressure of 58 atmospheres. Stirring at −10° C. was continued for an additional 1½ hours.

The reaction mixture was placed under a vacuum and the hydrogen fluoride was removed at 20° C. Ether and aqueous sodium bicarbonate were added to this crude product. Then the ether layer was separated, dried and distilled to give 29 grams (91% yield) of isopropyl isopropoxyacetate b.p. 91° C./5mm Hg.

EXAMPLE 5

The procedure of example 1 was repeated, except that the temperature rose from −17 to +20° C. over the 50 minutes of the run. Carbon monoxide uptake was completed in 10 minutes. The product was worked up as in Example 4, to give 78% isopropyl isopropoxyacetate and 12% isopropoxyacetic acid.

EXAMPLE 6

This example was carried out essentially the same as in Example 4, except that 9 grams of trioxane (0.3 mol of formaldehyde) was charged to the reactor and the temperature rose from −27° C. to +19° C. over the 60 minutes of the run. Carbon monoxide uptake was completed in about 30 minutes. Work-up was similar to that for Example 4, 75% isopropyl isopropoxyacetate, 6% isopropyl glycolate and 12% isopropylglycolyl isopropoxyacetate were obtained.

EXAMPLE 7

The apparatus of Example 1 was charged with 6 grams of trioxane (0.2 mols), 26.4 grams of isopropyl alcohol (0.44 mols), and 50 grams of hydrogen fluoride (2.5 mols). The autoclave was pressured to 68 atmospheres with carbon monoxide at 0° C. Stirring of the reaction mixture was continued for 60 minutes, although the carbon monoxide uptake was completed within 10 minutes. Analysis showed complete conversion of formaldehyde, with a 70% yield of isopropyl isopropoxyacetate and a 30% yield of isopropoxyacetic acid.

EXAMPLE 8

The reactor of Example 1 was charged as in Example 6. The carbon monoxide was charged to a pressure of 68 atmospheres. The reaction was run for 30 minutes at 20°–30° C. Carbon monoxide uptake was completed in 15 minutes. The reaction mixture was stripped of hydrogen fluoride at 100° C., to give a crude product containing 67% glycolic acid and 30% isopropoxyacetic acid.

Examples 1 and 2 gave excellent results when following the conditions specified by the invention. Example 3 shows that even though the time of reaction was substantially longer than for Examples 1 and 2, the results were poor because of the low reaction temperature of −30° C.

Example 4 illustrates the preferred method of recovering pure isopropyl isopropoxyacetate. Examples 5 and 6 show the reaction taking place while the temperature is allowed to increase throughout the run. Since the reaction is completed in about 10 to 30 minutes, and before the temperature reaches too high a value, reasonable yields of product are obtained. In Example 7, 30% of the product was isopropoxyacetic acid which is readily esterified to an isopropoxyacetate by reaction with an alcohol. This example is at the high end of the temperature range. Example 8 gives very poor yields of isopropoxyacetic acid and derivatives at 20° to 30° C., i.e., at temperatures higher than specified by the present invention.

What is claimed is:

1. Process for producing an alkyl alkoxyacetate from a secondary alcohol containing not more than 6 carbon atoms, which comprises contacting in a reaction zone said secondary alcohol with carbon monoxide and formaldehyde in the presence of hydrogen fluoride catalyst, under reaction conditions effective to produce the alkyl alkoxyacetate, including a temperature in the range 5° C. to −20° C., a carbon monoxide partial pressure of 0.5 to 275 atm.

2. Process according to claim 1, wherein the proportions of alcohol and formaldehyde contacted in the reaction zone are in the ratio of 2–15 mols alcohol for each mol of formaldehyde in the presence of 5 to 20 mols of hydrogen fluoride for each mol of formaldehyde and wherein the carbon monoxide partial pressure is in the range 50 to 70 atmospheres.

3. Process according to claim 2 wherein the mol ratio of alcohol to formaldehyde is in the ratio 2.5 to 10 mols alcohol for each mol of formaldehyde, and the hydrogen fluoride is present in a ratio of 8 to 15 mols per mol of formaldehyde.

4. Process according to claim 3 wherein the alcohol is selected from the group consisting of isopropyl alcohol and secondary butyl alcohol.

5. Process according to claim 4 wherein the alcohol is isopropyl alcohol.

* * * * *

UNITED STATES PATENT AND TRADEMARK OFFICE
CERTIFICATE OF CORRECTION

PATENT NO. : 4,308,397
DATED : December 29, 1981
INVENTOR(S) : SHIGETO SUZUKI

It is certified that error appears in the above–identified patent and that said Letters Patent are hereby corrected as shown below:

ABSTRACT

Line 3, "5°C" should read -- -5°C --.

Col. 4, line 41, "5°C" should read -- -5°C --.

Signed and Sealed this

Fourth Day of May 1982

[SEAL]

Attest:

GERALD J. MOSSINGHOFF

*Attesting Officer*     *Commissioner of Patents and Trademarks*